United States Patent
Sakanishi et al.

(10) Patent No.: US 10,351,513 B2
(45) Date of Patent: Jul. 16, 2019

(54) THICKENING AND STABILIZING AGENT, AND THICKENING AND STABILIZING COMPOSITION USING SAME

(71) Applicants: DAICEL CORPORATION, Osaka-shi, Osaka (JP); YAMAGUCHI UNIVERSITY, Yamaguchi-shi, Yamaguchi (JP)

(72) Inventors: Yuichi Sakanishi, Tokyo (JP); Takashi Saeki, Ube (JP); Mami Itoh, Ube (JP)

(73) Assignees: DAICEL CORPORATION, Osaka-Shi (JP); YAMAGUCHI UNIVERSITY, Yamaguchi-Shi (JP)

( * ) Notice: Subject to any disclaimer, the term of this patent is extended or adjusted under 35 U.S.C. 154(b) by 0 days.

(21) Appl. No.: 15/528,403

(22) PCT Filed: Nov. 10, 2015

(86) PCT No.: PCT/JP2015/081634
§ 371 (c)(1),
(2) Date: May 19, 2017

(87) PCT Pub. No.: WO2016/080248
PCT Pub. Date: May 26, 2016

(65) Prior Publication Data
US 2017/0320814 A1    Nov. 9, 2017

(30) Foreign Application Priority Data
Nov. 20, 2014    (JP) ................ 2014-235372

(51) Int. Cl.
| | |
|---|---|
| *C09D 7/43* | (2018.01) |
| *A23L 29/20* | (2016.01) |
| *C07C 235/74* | (2006.01) |
| *A61K 8/42* | (2006.01) |
| *A61K 47/18* | (2017.01) |
| *C09K 3/00* | (2006.01) |
| *A61Q 19/00* | (2006.01) |

(52) U.S. Cl.
CPC ............ *C07C 235/74* (2013.01); *A23L 29/20* (2016.08); *A61K 8/42* (2013.01); *A61K 47/18* (2013.01); *A61Q 19/00* (2013.01); *C09D 7/43* (2018.01); *C09K 3/00* (2013.01); *A23V 2002/00* (2013.01); *A61K 2800/10* (2013.01); *A61K 2800/48* (2013.01)

(58) Field of Classification Search
CPC .................................................. C07C 235/74
See application file for complete search history.

(56) References Cited

U.S. PATENT DOCUMENTS 5,973,076 A * 10/1999 Yoshimura .............. C08K 5/20
                                                    524/186
2014/0341960 A1    11/2014 Hattori et al.
2015/0376119 A1    12/2015 Sakanishi et al.
2016/0074304 A1     3/2016 Hattori et al.

FOREIGN PATENT DOCUMENTS

| EP | 3 000 8585 A1 | 3/2016 |
|---|---|---|
| JP | 1-163111 A | 6/1989 |
| JP | 2009-155592 A | 7/2009 |
| JP | 2010-111761 A | 5/2010 |
| JP | 6-192496 A | 11/2014 |
| JP | 2 813 558 A1 | 12/2014 |
| WO | WO 2013/118921 A1 | 8/2013 |
| WO | WO 2014/123110 A1 | 8/2014 |
| WO | WO 2014/189014 A1 | 11/2014 |
| WO | WO 2015/174343 A1 | 11/2015 |
| WO | WO 2015/190433 A1 | 12/2015 |

OTHER PUBLICATIONS

Extended European Search Report dated Apr. 24, 2018, in European Patent Application No. 15861230.9.
International Search Report for PCT/JP2015/081634 dated Jan. 12, 2016.
Written Opinion of the International Searching Authority for PCT/JP2015/081634 (PCT/ISA/237) dated Jan. 12, 2016.

* cited by examiner

*Primary Examiner* — Ana Z Muresan
(74) *Attorney, Agent, or Firm* — Birch, Stewart, Kolasch & Birch, LLP

(57) ABSTRACT

Provided are: a compound, a thickening/stabilizing agent including the compound, a thickened/stabilized composition including the thickening/stabilizing agent and a fluid organic substance, and a method for producing the thickened/stabilized composition, where the compound effectively thickens the fluid organic substance to a desired viscosity and effectively uniformly stabilizes the formulation of the composition containing the fluid organic substance via thickening of the fluid organic substance. The thickening/stabilizing agent according to the present invention includes a compound represented by Formula (1):

$$(R^2-HNOC)_{4-n}-R^1-(CONH-R^3)_n \quad (1)$$

where $R^1$ is a group resulting from removing four hydrogen atoms from the structural formula of butane; $R^2$ and $R^3$ are different from each other and are aliphatic hydrocarbon groups each containing 4 or more carbon atoms; and n is an integer of 1 to 3.

6 Claims, No Drawings

THICKENING AND STABILIZING AGENT, AND THICKENING AND STABILIZING COMPOSITION USING SAME

TECHNICAL FIELD

The present invention relates to: a novel compound that has the property of thickening/stabilizing fluid organic substances such as oils; a thickening/stabilizing agent including the compound; and a thickened/stabilized composition containing the compound. This application claims priority to Japanese Patent Application No. 2014-235372, filed Nov. 20, 2014 to Japan, the entire contents of which are incorporated herein by reference.

BACKGROUND ART

Liquid thickening/stabilizing techniques are industrially very important. For example, thickening/stabilizing of aqueous components in metastable emulsions, such as mayonnaise and salad dressing, allows the metastable emulsions to maintain their emulsion states stably over a long time. For the thickening/stabilizing techniques, various thickening/stabilizing agents have been developed. For example, alkyl acrylate copolymers are known as thickening/stabilizing agents for aqueous media (aqueous vehicles).

In contrast, 12-hydroxystearic acid is known as a thickening/stabilizing agent for fluid organic substances such as oily media and other organic substances having fluidity (e.g., Patent Literature (PTL) 1), where 12-hydroxystearic acid is mainly used for waste disposal of edible oils. However, 12-hydroxystearic acid is unadjustable in degree of gelling and can only bring the target component into either a completely solidified state or a liquid state as remaining as intact.

CITATION LIST

Patent Literature

PTL 1: Japanese Unexamined Patent Application Publication (JP-A) No. H01-163111

SUMMARY OF INVENTION

Technical Problem

Accordingly, the present invention has an object to provide a compound which effectively thickens a fluid organic substance to a desired viscosity, and which effectively uniformly stabilizes the formulation of a composition containing the fluid organic substance by thickening the fluid organic substance.

The present invention has another object to provide a thickening/stabilizing agent containing the compound, a thickened/stabilized composition which is thickened and/or stabilized by the thickening/stabilizing agent, and a method for producing the thickened/stabilized composition.

Solution to Problem

After intensive investigations to achieve the objects, the inventors of the present invention found that compounds having a structure represented by Formula (1) below, when selectively used according to the type of a fluid organic substance, can thicken the fluid organic substance to a desired viscosity and can uniformly stabilize a composition containing the fluid organic substance. Namely, the inventors found that the compounds can eliminate or minimize sedimentation, local aggregation, and/or concentration (enrichment) of the composition and can stably maintain the uniform state of the composition. The present invention has been made on the basis of these findings.

Specifically, the present invention provides a compound represented by Formula (1):

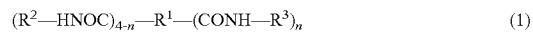
$$(R^2-HNOC)_{4-n}-R^1-(CONH-R^3)_n \qquad (1)$$

where $R^1$ is a group resulting from removing four hydrogen atoms from a structural formula of butane; $R^2$ and $R^3$ are different from each other and are aliphatic hydrocarbon groups each containing 4 or more carbon atoms; and n is an integer of 1 to 3.

The present invention also provides a thickening/stabilizing agent including the compound.

The present invention also provides a thickened/stabilized composition including the thickening/stabilizing agent and a fluid organic substance.

In addition and advantageously, the present invention provides a method for producing a thickened/stabilized composition. The method includes the step of dissolving the thickening/stabilizing agent and a fluid organic substance mutually in each other, wherethrough the thickened/stabilized composition is given.

Specifically, the present invention relates to the followings.

(1) A compound represented by Formula (1):

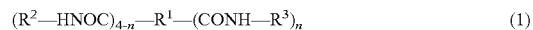
$$(R^2-HNOC)_{4-n}-R^1-(CONH-R^3)_n \qquad (1)$$

where $R^1$ is a group resulting from removing four hydrogen atoms from the structural formula of butane; $R^2$ and $R^3$ are different from each other and are aliphatic hydrocarbon groups each containing 4 or more carbon atoms; and n is an integer of 1 to 3.

(2) The compound according to (1), in which $R^2$ and $R^3$ in Formula (1) are a combination of $C_4$-$C_{20}$ branched chain alkyl with $C_4$-$C_{20}$ linear alkyl or linear alkenyl.

(3) The compound according to one of (1) and (2), in which the compound represented by Formula (1) is at least one compound selected from compounds represented by Formulae (1-1) to (1-5).

(4) The compound according to one of (1) and (2), in which the compound represented by Formula (1) is at least one of the compound represented by Formula (1-1) and the compound represented by Formula (1-2).

(5) A thickening/stabilizing agent including the compound according to any one of (1) to (4).

(6) The thickening/stabilizing agent according to (5), in which the thickening/stabilizing agent contains the compound represented by Formula (1) in a content of 60 weight percent or more of the total amount of the thickening/stabilizing agent.

(7) A thickened/stabilized composition including the thickening/stabilizing agent according to one of (5) and (6), and a fluid organic substance.

(8) The thickened/stabilized composition according to (7), in which the fluid organic substance is at least one compound selected from hydrocarbon oils, ethers, halogenated hydrocarbons, petroleum components, animal and vegetable oils, silicone oils, esters, aromatic carboxylic acids, and pyridine.

(9) The thickened/stabilized composition according to one of (7) and (8), in which the thickened/stabilized composition contains the thickening/stabilizing agent in a content of 0.1 to 100 parts by weight per 1000 parts by weight of the fluid organic substance.

(10) The thickened/stabilized composition according to any one of (7) to (9), in which the thickened/stabilized composition has a viscosity of 0.1 to 20 Pa·s as measured at 25° C. and at a shear rate of 10 s$^{-1}$.

(11) A method for producing a thickened/stabilized composition, the method including the step of dissolving the thickening/stabilizing agent according to one of (5) and (6) and a fluid organic substance mutually in each other, wherethrough the thickened/stabilized composition according to any one of (7) to (10) is given.

Advantageous Effects of Invention

The compounds represented by Formula (1) according to the present invention, via mutual dissolution in a fluid organic substance, can readily thicken the fluid organic substance, can uniformly stabilize the formulation of a composition containing the fluid organic substance, and can impart dispersion stability to the composition. The fluid organic substance, when thickened/stabilized by any of the compounds represented by Formula (1) according to the present invention, has an increased viscosity and can stably maintain such a state that its formulation is uniformized. The compounds represented by Formula (1) according to the present invention are therefore advantageously usable as thickening/stabilizing agents typically for cosmetics, coating materials, foodstuffs, and pharmaceutical preparations, can adjust the viscosities of these substances within desired ranges, can maintain their formulations uniformly, and allow them to have better usability.

DESCRIPTION OF EMBODIMENTS

Compound Represented by Formula (1)

Compounds according to the present invention are represented by Formula (1):

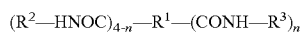

(1)

In the formula, R$^1$ is a group resulting from removing four hydrogen atoms from the structural formula of butane; R$^2$ and R$^3$ are different from each other and are aliphatic hydrocarbon groups each containing 4 or more carbon atoms; and n is an integer of 1 to 3.

Non-limiting examples of the compounds represented by Formula (1) include compounds represented by Formulae below. In the formulae, R$^2$ and R$^3$ are as defined above. When two or more occurrences of R$^2$ are present in the formulae, they represent an identical group. This is also true for R$^3$.

[Chem. 1]

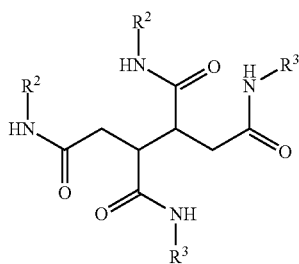

(1-1)

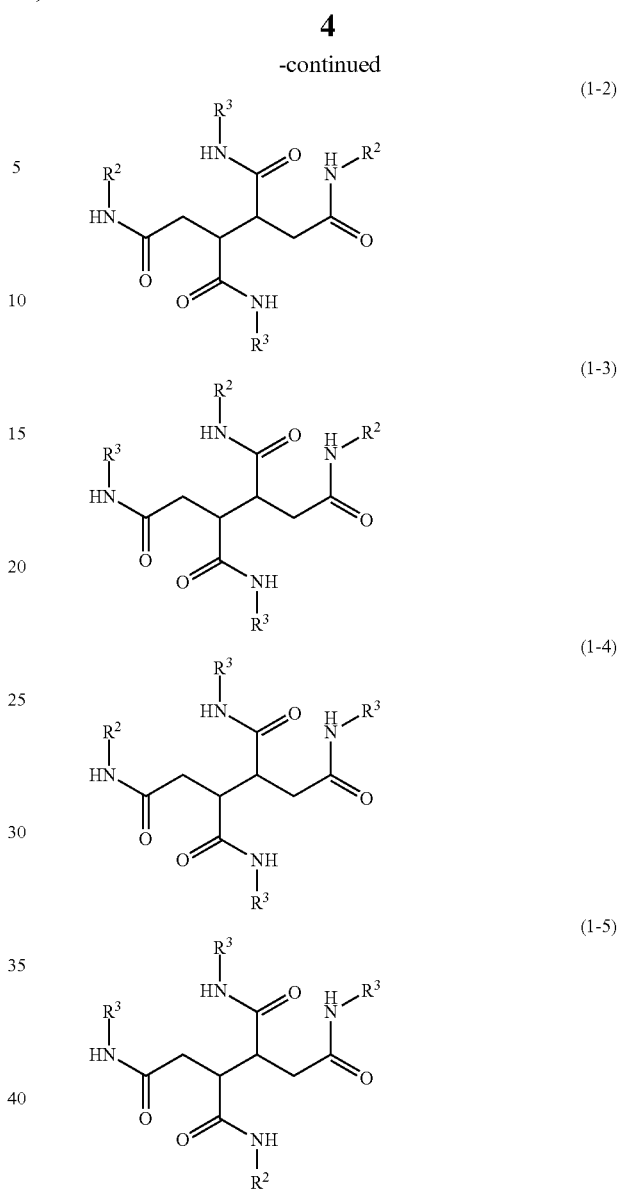

Of the compounds represented by Formula (1), at least one of the compounds represented by Formula (1-1) and the compounds represented by Formula (1-2) is preferred, because these compounds have excellent solubility with respect to a fluid organic substance. In addition, the compounds can advantageously impart pseudoplastic behavior and a high storage modulus to a fluid organic substance, while maintaining the transparency of the fluid organic substance when the fluid organic substance is transparent.

R$^2$ and R$^3$ are different from each other and are aliphatic hydrocarbon groups each containing 4 or more carbon atoms. Non-limiting examples of R$^2$ and R$^3$ include linear or branched chain alkyls containing 4 to about 20 (preferably 6 to 18, and particularly preferably 8 to 18) carbon atoms, such as butyl, pentyl, hexyl, octyl, 2-ethylhexyl, decyl, lauryl, myristyl, stearyl, and nonadecyl; linear or branched chain alkenyls containing 2 to about 20 (preferably 6 to 18, and particularly preferably 12 to 18) carbon atoms, such as 2-butenyl, 2-pentenyl, 2-hexenyl, 3-hexenyl, 4-hexenyl, 5-hexenyl, 7-octenyl, 9-decenyl, 11-dodecenyl, and oleyl; and linear or branched chain alkynyls containing 4 to about 20 (preferably 6 to 18, and particularly preferably 12 to 18) carbon atoms, such as hexynyl, octynyl, decynyl, pentadecynyl, and octadecynyl.

Of the compounds represented by Formula (1), particularly preferred are compounds in which one of $R^2$ and $R^3$ is $C_4$-$C_{20}$ (more preferably $C_6$-$C_{18}$, and particularly preferably $C_8$-$C_{18}$) branched chain alkyl, and the other is $C_4$-$C_{20}$ (more preferably $C_6$-$C_{18}$, and particularly preferably $C_{12}$-$C_{18}$) linear alkyl or linear alkenyl. These compounds are preferred because of having excellent solubility with respect to a fluid organic substance and being capable of effectively thickening the fluid organic substance.

The compounds represented by Formula (1) may each be produced typically by any of the following methods 1 and 2.

The method 1 includes allowing a butanetetracarboxylic acid to react with thionyl chloride to give a butanetetracarboxylic acid tetrachloride, and allowing the obtained butanetetracarboxylic acid tetrachloride to react with amines ($R^2$—$NH_2$ and $R^3$—$NH_2$; where $R^2$ and $R^3$ are as defined above).

The method 2 includes allowing a butanetetracarboxylic acid dianhydride to react with an amine (1) ($R^2$—$NH_2$; where $R^2$ is as defined above) to give an amic acid, and condensing the amic acid further with an amine (2) ($R^3$—$NH_2$; where $R^3$ is as defined above) using a condensing agent.

Non-limiting examples of the amines ($R^2$—$NH_2$ and $R^3$—$NH_2$) for use in the production method 1 include amines in which $R^2$ and $R^3$ are differently $C_4$ or higher (preferably $C_4$-$C_{18}$) aliphatic hydrocarbon groups (preferably linear or branched chain alkyls, alkenyls, or alkynyls), such as n-butylamine, s-butylamine, t-butylamine, hexylamine, octylamine, 2-ethylhexylamine, decylamine, laurylamine, myristylamine, stearylamine, and oleylamine.

In the production method 1, the reaction between the butanetetracarboxylic acid tetrachloride (such as 1,2,3,4-butanetetracarboxylic acid tetrachloride) and the amines can be performed typically by adding the butanetetracarboxylic acid tetrachloride dropwise to a system containing the amines.

The amines may be used in an amount (in a total amount of $R^2$—$NH_2$ and $R^3$—$NH_2$) of typically about 4 to about 8 moles, and preferably 4 to 6 moles, per mole of the butanetetracarboxylic acid tetrachloride. Control of the proportions of (ratio between) $R^2$—$NH_2$ and $R^3$—$NH_2$ to be used can control the numbers of the CONH—$R^2$ group and the CONH—$R^3$ group in the resulting compound represented by Formula (1).

The reaction between the butanetetracarboxylic acid tetrachloride and the amines can be performed in the presence of, or in the absence of, a solvent. Non-limiting examples of the solvent include saturated or unsaturated hydrocarbon solvents such as pentane, hexane, heptane, octane, and petroleum ether; aromatic hydrocarbon solvents such as benzene, toluene, and xylenes; halogenated hydrocarbon solvents such as methylene chloride, chloroform, 1,2-dichloroethane, chlorobenzene, and bromobenzene; ether solvents such as diethyl ether, diisopropyl ether, dibutyl ether, tetrahydrofuran, dioxane, 1,2-dimethoxyethane, and cyclopentyl methyl ether; nitrile solvents such as acetonitrile and benzonitrile; sulfoxide solvents such as dimethyl sulfoxide; sulfolane solvents such as sulfolane; amide solvents such as dimethylformamide; and high-boiling solvents such as silicone oils. Each of them may be used alone or in combination.

The solvent(s) may be used in an amount of typically about 50 to about 300 weight percent, and preferably 100 to 250 weight percent, relative to the total amount of the butanetetracarboxylic acid tetrachloride and the amines. The solvent(s), if used in an amount greater than the range, tends to cause a lower reaction rate because of lower concentrations of the reaction components.

The reaction (i.e., dropping) between the butanetetracarboxylic acid tetrachloride and the amines is generally performed at normal atmospheric pressure. The reaction atmosphere (i.e., atmosphere upon dropping) is not limited, as long as not adversely affecting the reaction, and may be selected freely from any atmospheres such as air atmosphere, nitrogen atmosphere, and argon atmosphere. The reaction temperature (i.e., temperature upon dropping) is typically about 30° C. to about 60° C. The reaction time (i.e., dropping time) is typically about 0.5 to about 20 hours. The method may further include an aging step after the completion of reaction (i.e., dropping). When the method further includes the aging step, the aging may be performed at a temperature of typically about 30° C. to about 60° C. for a time of typically about 1 to about 5 hours. The reaction may be performed according to any technique or system such as batch system, semi-batch system, or continuous system.

The reaction product obtained after the completion of the reaction can be separated/purified by a separation means such as filtration, concentration, distillation, extraction, crystallization, adsorption, recrystallization, or column chromatography, or a separation means as any combination of them.

The production method 2 can produce the compound represented by Formula (1) typically by charging the butanetetracarboxylic acid dianhydride (such as 1,2,3,4-butanetetracarboxylic acid-1,2:3,4-dianhydride), the amine (1), and an after-mentioned solvent into a system, aging the materials to give an amic acid, subsequently charging the amine (2) and the condensing agent (such as a carbodiimide or a salt thereof), and aging the materials.

Examples of the amines (1) and (2) for use herein include compounds as with the amines for use in the production method 1.

The amine (1) may be used in an amount of typically about 2 to about 4 moles, and preferably 2 to 3 moles, per mole of the butanetetracarboxylic acid dianhydride. The amine (2) may be used in an amount of typically about 2 to about 4 moles, and preferably 2 to 3 moles, per mole of the butanetetracarboxylic acid dianhydride.

The carbodiimide is expressed by the formula:

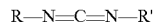

In the formula, R and R' are each independently selected typically from $C_3$-$C_8$ linear or branched chain alkyl and 3- to 8-membered cycloalkyl, each of which may have a heteroatom-containing substituent. R and R' may be identical or different. R and R' may be linked to each other to form a ring with the —N=C=N— group.

Non-limiting examples of the $C_3$-$C_8$ linear or branched chain alkyl include propyl, isopropyl, butyl, isobutyl, s-butyl, t-butyl, pentyl, isopentyl, s-pentyl, t-pentyl, hexyl, isohexyl, s-hexyl, and t-hexyl.

Non-limiting examples of the 3- to 8-membered cycloalkyl include cyclopropyl, cyclobutyl, cyclopentyl, cyclohexyl, and cyclooctyl.

Non-limiting examples of the heteroatom-containing substituent include nitrogen atom-containing substituents exemplified by amino, and di($C_1$-$C_3$)alkyl-aminos such as dimethylamino.

Non-limiting examples of the carbodiimide include diisopropylcarbodiimide, dicyclohexylcarbodiimide, and N-(3- dimethylaminopropyl)-N'-ethylcarbodiimide. Non-limiting examples of the salt of the carbodiimide include hydrochlorides such as N-(3-dimethylaminopropyl)-N'-ethylcarbodiimide hydrochloride.

The carbodiimide may be used in an amount of typically about 2 to about 6 moles, and preferably 2 to 4 moles, per mole of the butanetetracarboxylic acid dianhydride.

Preferred examples of the solvent for use herein include proton-acceptor solvents such as pyridine, triethylamine, and tributylamine, because these solvents excellently dissolve the amic acid therein. Each of them may be used alone or in combination.

The solvent may be used in an amount of typically about 50 to about 300 weight percent, and preferably 100 to 250 weight percent, relative to the total amount of the amic acid. The solvent, if used in an amount greater than the range, tends to cause a lower reaction rate because of lower concentrations of the reaction components.

The reaction is generally performed at normal atmospheric pressure. The reaction atmosphere is not limited, as long as not adversely affecting the reaction, and may be any atmosphere such as air atmosphere, nitrogen atmosphere, or argon atmosphere. The aging (reaction) may be performed at a temperature of typically about 30° C. to about 70° C. The aging of the butanetetracarboxylic acid dianhydride and the amine may be performed for a time of typically about 0.5 to about 5 hours, and the aging of the amic acid and the amine may be performed for a time of typically about 0.5 to about 20 hours. The reaction may be performed according to any system such as batch system, semi-batch system, or continuous system.

After the completion of the reaction, the resulting reaction product may be separated/purified by a separation means such as filtration, concentration, distillation, extraction, crystallization, adsorption, recrystallization, or column chromatography, or a separation means as any combination of them.

The compounds represented by Formula (1) can undergo self-association via hydrogen bonding at amide bond sites to form a fibrous self-assembled structure. The compounds represented by Formula (1), when mutually dissolved in a fluid organic substance, can thicken the fluid organic substance and uniformly stabilize a composition containing the fluid organic substance. This is because the groups $R^2$ and $R^3$ have affinity for such fluid organic substances. In addition, the compounds represented by Formula (1) have appropriate crystallinity because the groups $R^2$ and $R^3$ are different from each other. This allows the compounds to have excellent solubility in fluid organic substances and to be able to thicken/stabilize approximately any organic substances having fluidity without limitation. Namely, the compounds have wide selectivity for fluid organic substances to be thickened. When the fluid organic substance has transparency, the compounds can thicken/stabilize the fluid organic substance and can form a thickened/stabilized composition that is stable with time, while maintaining the transparency. The compounds are therefore useful typically as thickening/stabilizing agents (more specifically thickeners or stabilizers) for fluid organic substances. In contrast, of compounds represented by Formula (1), compounds in which the groups $R^2$ and $R^3$ are identical groups have excessively high crystallinity and can only bring the fluid organic substance into either a completely solidified (gelled) state or a liquid state as remaining as intact. Disadvantageously, these compounds tend to be readily crystallized by the interaction of side chains, are limited in fluid organic substances that can be thickened/stabilized, and are limited in selectivity for fluid organic substances to be thickened. These compounds may often become cloudy when mutually dissolved in fluid organic substances and may fail to maintain beautiful appearances. In addition, the resulting thickened/stabilized compositions are liable to have a decreasing viscosity with time.

Thickening/Stabilizing Agent

The thickening/stabilizing agent according to the present invention includes each of the compounds represented by Formula (1) alone or in combination.

The thickening/stabilizing agent according to the present invention may further include another thickening/stabilizing agent than the compounds represented by Formula (1). However, the thickening/stabilizing agent according to the present invention may contain the compound(s) represented by Formula (1) in a content of typically 0.5 weight percent or more, preferably 1 weight percent or more, more preferably 10 weight percent or more, particularly preferably 30 weight percent or more, furthermore preferably 60 weight percent or more, and most preferably 80 weight percent or more, of the total amount (100 weight percent) of the thickening/stabilizing agent. When the thickening/stabilizing agent contains two or more compounds represented by Formula (1), the term "content" refers to the total content of them. The upper limit of the content of the compound(s) represented by Formula (1) is 100 weight percent. The thickening/stabilizing agent, if containing the compound(s) represented by Formula (1) in a content out of the range, tends to hardly thicken a fluid organic substance, or tends to hardly uniformly stabilize a composition containing the fluid organic substance.

As used herein, the term "thickening/stabilizing agent" is a concept which refers to a compound or compounds being dissolved in a fluid organic substance to develop viscosity and which also includes thickeners that impart viscosity to the fluid organic substance; and stabilizers that increase the viscosity of a composition containing the fluid organic substance in order to uniformly stabilize the composition. Non-limiting examples of the other thickening/stabilizing agent include base materials, hydroxyfatty acids, acrylic polymers, oligomer esters (such as dextrin fatty acid esters), and particles of metal oxides.

The thickening/stabilizing agent according to the present invention may be used in a form selected from various forms such as powder, granular, liquid, and milky lotion forms.

Assume that the thickening/stabilizing agent according to the present invention and a fluid organic substance are dissolved mutually in each other (preferably, the thickening/stabilizing agent is mixed with the fluid organic substance and heated to dissolve them in each other, and the resulting mixture is cooled). This can thicken the fluid organic substance and allows the fluid organic substance to have a desired viscosity according to the intended use within the range of from greater than 1 time to 10000 times (preferably from greater than 10 times to 10000 times, and particularly preferably from 10 to 1000 times).

Thickened/Stabilized Composition

The thickened/stabilized composition according to the present invention is a composition including the thickening/stabilizing agent and a fluid organic substance, in which the thickening/stabilizing agent thickens the fluid organic substance, or a composition including the thickening/stabilizing agent and a fluid organic substance, in which the thickening/stabilizing agent thickens the fluid organic substance to thereby uniformly stabilize the formulation of the composition.

The thickened/stabilized composition according to the present invention can be produced through the step of dissolving the thickening/stabilizing agent and the fluid organic substance in each other. More specifically, the composition can be produced by mixing the thickening/stabilizing agent with the whole quantity of the fluid organic substance, heating the mixture to dissolve the two components in each other, and cooling the mixture. The composition can also be produced by mixing the thickening/stabilizing agent with part of the fluid organic substance, heating the mixture to dissolve the two components in each other, cooling the mixture to give a composition, and mixing the composition with the remainder of the fluid organic substance.

The fluid organic substance (flowable organic substance) is preferably selected from organic substances having a viscosity of typically less than 0.1 Pa·s, where the viscosity is a viscosity ($\eta$) as measured at 25° C. and at a shear rate of 10 $s^{-1}$ using a rheometer. Such fluid organic substances are exemplified by, but are not limited to, hydrocarbon oils such as hexane, cyclohexane, isododecane, benzene, toluene, poly-α-olefins, and liquid paraffin; ethers such as tetrahydrofuran; halogenated hydrocarbons such as carbon tetrachloride and chlorobenzene; petroleum components such as kerosene, gasoline, light oil, and heavy oil; animal and vegetable oils such as sunflower oil, olive oil, soybean oil, corn oil, castor oil, beef tallow, jojoba oil, and squalane; silicones such as dimethylpolysiloxanes and methylphenylpolysiloxanes; esters such as octyldodecyl oleate, cetyl octanoate, cetyl ethylhexanoate, glyceryl triisooctanoate, neopentyl glycol diisooctanoate, and tricaprylin; aromatic carboxylic acids; and pyridine. Each of them may be used alone or in combination.

The thickening/stabilizing agent may be mixed (used) in an amount of typically 0.1 to 100 parts by weight, preferably 0.5 to 90 parts by weight, particularly preferably 1 to 80 parts by weight, and most preferably 1 to 30 parts by weight, per 1000 parts by weight of the fluid organic substance, while the amount may vary depending typically on the type of the fluid organic substance. The thickening/stabilizing agent, when mixed (used) in an amount within the range, gives the thickened/stabilized composition according to the present invention.

The thickened/stabilized composition according to the present invention may further contain one or more other components within the ranges not adversely affecting the advantageous effects of the present invention, in addition to the thickening/stabilizing agent and the fluid organic substance. Non-limiting examples of the other components include regular compounds (such as medicinal components, pigments, and flavors) to be contained in compositions that require thickening/stabilization, such as cosmetics, coating materials, foodstuffs, and pharmaceutical preparations.

The temperature at which the mutual dissolution is performed may be selected as appropriate according to the types of the thickening/stabilizing agent and the fluid organic substance to be used, and is not limited as long as being such a temperature at which the thickening/stabilizing agent and the fluid organic substance can be dissolved in each other. However, the temperature is preferably not higher than 100° C., and, when the fluid organic substance has a boiling point of 100° C. or lower, is preferably a temperature around the boiling point.

The cooling after mutual dissolution is not limited, as long as being capable of cooling down to room temperature (for example, about 25° C. or lower). The composition may be allowed to stand to cool at room temperature gradually, or may be rapidly cooled typically via ice cooling.

The thickened/stabilized composition according to the present invention has a viscosity of typically 0.1 to 20 Pa·s, preferably 0.5 to 10 Pa·s, and particularly preferably 0.5 to 5 Pa·s, where the viscosity is a viscosity ($\eta$) as measured at 25° C. and at a shear rate of 10 $s^{-1}$ using a rheometer. The viscosity can be adjusted as appropriate according to the intended use within the range of from greater than 1 time to 10000 times (preferably from greater than 10 times to 10000 times, and particularly preferably from greater than 10 times to 1000 times) the viscosity of the raw material fluid organic substance.

The thickened/stabilized composition according to the present invention is not limited, as long as being a composition which contains a fluid organic substance and in which the fluid organic substance is desired to be thickened/stabilized. Non-limiting examples of the thickened/stabilized composition include cosmetics, coating materials, foodstuffs, and pharmaceutical preparations.

EXAMPLES

The present invention will be illustrated in further detail with reference to several examples below. It should be noted, however, that the examples are by no means intended to limit the scope of the present invention.

Example 1: Synthesis of Thickening/Stabilizing Agent (1) (1,2,3,4-butanetetracarboxylic acid di(2-ethylhexylamide)di(oleylamide))

Into a 100-mL four-neck separable flask equipped with a Dimroth condenser, a nitrogen inlet, a dropping funnel, and a thermocouple, 20 mL of pyridine, 4.2 g (0.021 mol) of 1,2,3,4-butanetetracarboxylic acid-1,2:3,4-dianhydride, and 11.3 g (0.042 mol) of oleylamine were charged, followed by aging for 3 hours at a set system internal temperature of 50° C.

Subsequently 5.4 g (0.042 mol) of 2-ethylhexylamine and 5.8 g (0.048 mol) of diisopropylcarbodiimide were charged, followed by aging for further 8 hours to give a crude mixture.

After removing low-boiling components on an evaporator therefrom, the crude mixture was washed with methanol and yielded a pale yellow wet powder. The obtained wet powder was subjected to recrystallization from $CHCl_3/CH_3OH$ (70/30 (v/v)) and yielded 16.7 g of 1,2,3,4-butanetetracarboxylic acid di(2-ethylhexylamide)di(oleylamide) (a mixture of 1,2,3,4-butanetetracarboxylic acid-1,4-di(2-ethylhexylamide)-2,3-di(oleylamide) and 1,2,3,4-butanetetracarboxylic acid-1,3-di(2-ethylhexylamide)-2,4-di(oleylamide)) in a yield of 83%. The structure of the reaction product was identified by $^1$H-NMR.

$^1$H-NMR (270 MHz, $CDCl_3$): δ 0.81-0.88 (m, 18H), 1.0-1.4 (m, 70H), 1.40-1.45 (m, 8H), 1.81-1.99 (m, 8H), 2.90-3.45 (m, 6H), 5.32-5.40 (m, 4H), 6.32 (m, 4H)

Comparative Example 1: Synthesis of Thickening/Stabilizing Agent (2) (1,2,3,4-butanetetracarboxylic acid tetraoleylamide)

A procedure similar to that in Example 1 was performed, except for using 11.3 g (0.042 mol) of oleylamine instead of 5.4 g (0.042 mol) of 2-ethylhexylamine, and yielded 20.9 g of 1,2,3,4-butanetetracarboxylic acid tetraoleylamide in a yield of 81%. The structure of the reaction product was identified by $^1$H-NMR.

$^1$H-NMR (270 MHz, CDCl$_3$): δ 0.81-0.88 (m, 12H), 1.0-1.4 (m, 104H), 1.40-1.45 (m, 8H), 1.81-1.99 (m, 8H), 2.90-3.45 (m, 6H), 5.32-5.40 (m, 8H), 6.32 (m, 4H)

Example 2

One cubic centimeter of each of fluid organic substances given in the table below was measured and placed in a test tube, combined and mixed with 10 mg of the thickening/stabilizing agent (1) obtained in Example 1, stirred with heating at 100° C. to dissolve the fluid organic substance and the thickening/stabilizing agent (1) in each other, cooled down to 25° C., and yielded a series of thickened/stabilized compositions. The fluid organic substances were liquid paraffin (viscosity: 0.14 Pa·s), isododecane (viscosity: 0.001 Pa·s), and cetyl octanoate (viscosity: 0.012 Pa·s), each of which has a boiling point of 100° C. or higher.

The obtained thickened/stabilized compositions had viscosities as follows.

Thickened/stabilized composition of liquid paraffin: 2.31 Pa·s

Thickened/stabilized composition of isododecane: 0.86 Pa·s

Thickened/stabilized composition of cetyl octanoate: 2.67 Pa·s

A thickening ratio was calculated according to the following expression, on the basis of which a thickening effect was evaluated according to the following evaluation criteria, and samples evaluated and scored as 4 or higher with respect to all the fluid organic substances were evaluated as having a good thickening effect (Good), and the other samples were evaluated as having a poor thickening effect (Poor).

Thickening ratio=(Viscosity of thickened/stabilized composition)/(Viscosity of fluid organic substance before thickening/stabilization)

Evaluation Criteria:
1: from greater than 1.0 time to 2.0 times
2: from greater than 2.0 times to 4.8 times
3: from greater than 4.8 times to 10 times
4: from greater than 10 times to 50 times
5: from greater than 50 times to 100 times
6: from greater than 100 times to 10000 times
7: greater than 10000 times The viscosities of the fluid organic substances before thickening/stabilization, and of the thickened/stabilized compositions were determined in the following manner. The measurement was performed using a viscosity/visco-elastometer (rheometer) (HAAKE RheoStress 600 (trade name)) equipped with a cone-and-plate sensor and a Peltier temperature controller. The cone-and-plate system in the sensor used had a diameter of 60 mm with a cone angle of 1°, or a diameter of 35 mm with a cone angle of 1°, 2°, or 4°. The viscosities were measured in a steady flow viscosity measurement mode at 25° C. and at different shear rates varying in a log scale from 0.001 to 100 s$^{-1}$, on the basis of which a viscosity curve was plotted. A viscosity at a shear rate of 10 s$^{-1}$ was determined from the viscosity curve, and this was defined as the viscosity in the present invention. Each plot employed values obtained at the time point when the torque value variation of the instrument was settled within the range of 5% and the data became stable.

Comparative Example 2

A procedure similar to that in Example 2 was performed, except for using the thickening/stabilizing agent (2) obtained in Comparative Example 1, instead of the thickening/stabilizing agent (1).

The results are collectively presented in the following table.

TABLE 1

| | | Example 2 Thickening/ stabilizing agent (1) | Comparative Example 2 Thickening/stabilizing agent (2) |
|---|---|---|---|
| Fluid organic substance | Liquid paraffin | 4 | Gelled (irreversibly) |
| | Isododecane | 6 | Partially gelled |
| | Cetyl octanoate | 6 | Gelled |
| Thickening effect | | Good | Poor |

The results demonstrate that the thickening/stabilizing agent according to the present invention can highly effectively thicken the fluid organic substances. In contrast, the thickening/stabilizing agent obtained in the comparative example could only bring the fluid organic substances into either a completely solidified (gelled) state or a liquid state as remaining as intact and failed to thicken the fluid organic substances to appropriate degrees.

INDUSTRIAL APPLICABILITY

The compounds represented by Formula (1) according to the present invention, via mutual dissolution in a fluid organic substance, can readily thicken the fluid organic substance, can uniformly stabilize the formulation of a composition containing the fluid organic substance, and can impart dispersion stability to the composition. A fluid organic substance, when thickened/stabilized by any of the compounds represented by Formula (1) according to the present invention, has an increased viscosity and can stably maintain such a state that its formulation is uniformized. The compounds represented by Formula (1) according to the present invention are therefore advantageously usable as thickening/stabilizing agents typically for cosmetics, coating materials, foodstuffs, and pharmaceutical preparation.

The invention claimed is:

1. A compound of Formula (1):

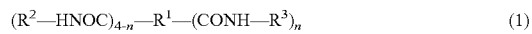

(R$^2$—HNOC)$_{4-n}$—R$^1$—(CONH—R$^3$)$_n$     (1)

wherein

R$^1$ is a group resulting from removing four hydrogen atoms from a structural formula of butane;

R$^2$ and R$^3$ are different from each other and are aliphatic hydrocarbon groups selected from the group consisting of C8-C18 branched chain alkyl, C8-C18 linear alkyl and C6-C18 linear alkenyl; and n is an integer of 1 to 3.

2. A thickening/stabilizing agent comprising the compound according to claim 1.

3. The compound according to claim 1, wherein the compound of Formula (1) is at least one compound selected from compounds of Formulae (1-1) and (1-2)

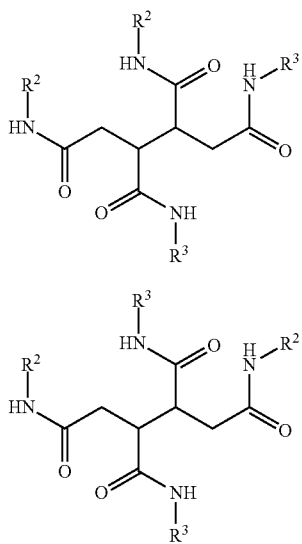

(1-1)

(1-2)

wherein $R^2$ and $R^3$ are different from each other and are aliphatic hydrocarbon groups selected from the group consisting of C8-C18 branched chain alkyl, C8-C18 linear alkyl and C6-C18 linear alkenyl.

4. The compound according to claim 1, wherein the compound of Formula (1) is 1,2,3,4-butanetetracarboxylic acid di(2-ethylhexylamide) di(oleylamide).

5. A thickened/stabilized composition comprising:
   the thickening/stabilizing agent according to claim 2; and
   a fluid organic substance.

6. A method for producing a thickened/stabilized composition, the method comprising the step of
   dissolving the thickening/stabilizing agent according to claim 2 and a fluid organic substance mutually in one another to make a thickened/stabilized composition.

* * * * *